(12) United States Patent
Gotz et al.

(10) Patent No.: US 8,849,823 B2
(45) Date of Patent: Sep. 30, 2014

(54) INTERACTIVE VISUALIZATION OF TEMPORAL EVENT DATA AND CORRELATED OUTCOMES

(75) Inventors: David Gotz, Purdys, NY (US); Krist Wongsuphasawat, Hawthorne, NY (US)

(73) Assignee: International Business Machines Corporation, Armonk, NY (US)

( * ) Notice: Subject to any disclaimer, the term of this patent is extended or adjusted under 35 U.S.C. 154(b) by 399 days.

(21) Appl. No.: 13/277,467

(22) Filed: Oct. 20, 2011

(65) Prior Publication Data

US 2013/0103719 A1  Apr. 25, 2013

(51) Int. Cl.
*G06F 19/00* (2011.01)
*G06T 11/20* (2006.01)

(52) U.S. Cl.
CPC ........... *G06T 11/206* (2013.01); *G06F 19/3487* (2013.01)
USPC ................ 707/736; 705/3; 715/771; 345/440

(58) Field of Classification Search
CPC .. G06T 17/005; G06T 11/206; G06F 19/3487
USPC ....................................................... 707/736
See application file for complete search history.

(56) References Cited

U.S. PATENT DOCUMENTS

| | | | |
|---|---|---|---|
| 7,499,046 B1 | 3/2009 | Wright et al. | |
| 2007/0127695 A1 | 6/2007 | Noyan et al. | |
| 2010/0060643 A1* | 3/2010 | Kolipaka et al. | 345/440 |
| 2010/0153870 A1 | 6/2010 | Hoffmann | |

OTHER PUBLICATIONS

D. Pharm et al., "Flow Map Layout," Proc. IEEE Symp. Information Visualization, pp. 219-224 (2005).*
K. K Wongsuphasawat et al., "LifeFlow: Visualizing an Overview of Event Sequences," Proc. Annual SIGCHI Conf. Human Factors in Computing Systems (CHI), pp. 1747-1756. May 7, 2011.*
K. Sugiyama et al., "Methods for Visual Understanding of Hierarchical System Structures," IEEE Trans. on Systems, Man, and Cybernetics, 11(2), 109-125 (1981).*
Bramsen, Doing Time: Inducing Temporal Graphs, Jun. 2006, pp. 1-51.*
P.A. McKee et al., "The Natural History of Congestive Heart Failure: The Framingham Study," The New England Journal of Medicine, 285(26): 1441-46 (1971).
Wongsuphasawat et al., "LifeFlow: Visualizing an Overview of Event Sequences", CHI, Vancouver, bc (2011).

(Continued)

*Primary Examiner* — Albert Phillips, III
(74) *Attorney, Agent, or Firm* — Ryan, Mason & Lewis, LLP (57) ABSTRACT

Methods and apparatus are provided for interactive visualization of temporal event data and correlated outcomes. The temporal event data comprises a plurality of entities undergoing one or more events. The temporal event data is aggregated and a flow graph is generated to represent the aggregated temporal event data. The flow graph comprises a directed acyclic graph having a plurality of nodes connected by edges, wherein each of the nodes represents a group of entities in a given state. A view of the flow graph is generated and then a visualization of the flow graph view can be rendered to a user. The user can interact with the flow graph view and the visualization and/or the flow graph view can be updated based on the user interactions. The flow graph is sliced into layers, wherein a given layer i contains all nodes with i events.

24 Claims, 7 Drawing Sheets

(56) References Cited

OTHER PUBLICATIONS

Phan et al., "Flow Map Layout", Infovis (2005), downloaded on Oct. 21, 2011.
http://.csse.monash.edu.au/~berndm/CSE460/Lectures/cse460-7.pdf.
Sugiyama at al., "Methods for Visual Understandings of Hierarchical System Structures", in IEEE Transactions in Systems, vol. smc-11, No. 2, pp. 109-125 (1981).
http://en.wikipedia.org/wiki/Flow_map, downloaded on Oct. 21, 2011.
John Corbett, "Charles Joseph Minard: Mapping Napoleon's March, 1861" http:/www.csiss.org/classics/content/58.

* cited by examiner

| PATIENT | OUTCOME | TIME-STAMPED SYMPTOMS | | | | | |
|---------|---------|----|----|----|----|----|----|
| A | 0 | $S_1$ | $S_2$ | | $S_4$ | $S_3$ | ... |
| B | 1 | $S_2$ | $S_1$ | $S_3$ | | | ... | $S_4$ |
| C | .85 | $S_2$ | $S_1$ | $S_3$ | | | ... | $S_5$ |

ND OF THE INVENTION

The present invention relates generally to the electrical, electronic and computer arts, and, more particularly, to techniques for aggregation and/or visualization of temporal event data.

BACKGROUND OF THE INVENTION

Temporal event data is common in many fields. Temporal event data typically comprises a set of entities undergoing various events, such as patients that are diagnosed with various symptoms or call center tickets that move from an initial call state to a resolution state. Electronic medical records (EMRs), for example, are proliferating throughout the healthcare system and contain a large amount of temporal disease events such as diagnosis dates and the onset dates for various symptoms. At major medical institutions, such as hospitals, insurance companies and large medical groups, these databases contain large amounts of historical patient data complete with patient profile information, structured observational data (such as diagnosis codes and medications), as well as unstructured physician notes.

The information in these databases can be useful in guiding the diagnosis of incoming patients or in clinical studies of a disease. The vast amount of information, however, can be overwhelming and makes these datasets difficult to analyze. Analyzing disease progression pathways in terms of these observed events, for example, can provide important insights into how diseases evolve over time. Moreover, correlating these pathways (i.e., flows) with the eventual outcomes of the corresponding patients can help clinicians understand how certain progression paths may lead to better or worse outcomes. For example, medical professionals are often interested in understanding how various symptoms of a given disease, and their order of onset, correlate with patient outcome.

A need therefore exists for methods and apparatus for temporal graph-based visualization of event data. A further need exists for methods and apparatus for aggregating the temporal event data to identify common states and transitions between states. In addition, a need exists for methods and apparatus for identifying correlations between these pathways with eventual outcomes.

SUMMARY OF THE INVENTION

Generally, methods and apparatus are provided for interactive visualization of temporal event data and correlated outcomes. The temporal event data comprises a plurality of entities undergoing one or more events, such as time-stamped entries indicating each time a patient is diagnosed with a given symptom.

According to one aspect of the invention, the temporal event data is aggregated and a flow graph is generated to represent the aggregated temporal event data. The flow graph comprises a directed acyclic graph having a plurality of nodes connected by edges, wherein each of the nodes represents a group of entities in a given state. A view of the flow graph is generated and then a visualization of the flow graph view can be rendered to a user. The user can interact with the flow graph view and the visualization anchor the flow graph view can be updated based on the user interactions. The user interactions comprise (i) structural interactions that require an update to the flow graph view and/or (ii) display interactions that require an update to the visualization.

The flow graph is sliced into layers, wherein a given layer i contains all nodes with i events. The flow graph optionally indicates event paths that lead to a given alignment point and event paths that lead from the alignment point.

In one exemplary implementation, each edge has an associated annotation indicating a number of entities that make the corresponding transition, the average time gap between the states, and the average outcome of the entities that make the corresponding transition. The edges in the flow graph and/or the visualization can be straightened. The number of overlapping edges and/or edge crossings in the flow graph and/or the visualization can be reduced. Edges in the visualization are visually encoded using at least a time edge and at least a link edge. The size of the time edge indicates a duration of the corresponding transition. The link edges connect an end of one of the time edges with a node to indicate a sequentiality of nodes.

In one exemplary implementation, nodes in the visualization are visually encoded using a given shape. An average outcome can be encoded using one or more of a distinct hash pattern and a distinct color, which optionally scales linearly between two values each representing a different extreme outcome. A position of a node in one direction can indicate a sequence of states. A size of a node in one direction can indicate a number of entities associated with the node.

A more complete understanding of the present invention, as well as further features and advantages of the present invention, will be obtained by reference to the following detailed description and drawings.

DETAILED DESCRIPTION OF PREFERRED EMBODIMENTS

The present invention provides a tool for aggregating and visualizing temporal event data. According to one aspect of the invention, the aggregation of temporal event data allows common states to be identified, as well as the various transitions between states. In addition, methods and apparatus are provided for identifying correlations between pathways between states and the eventual outcomes. While the present invention is illustrated herein in the context of exemplary electronic medical records (EMRs), the present invention can be employed to aggregate and/or visualize any temporal event data, as would be apparent to a person of ordinary skill in the art.

Figure 7:
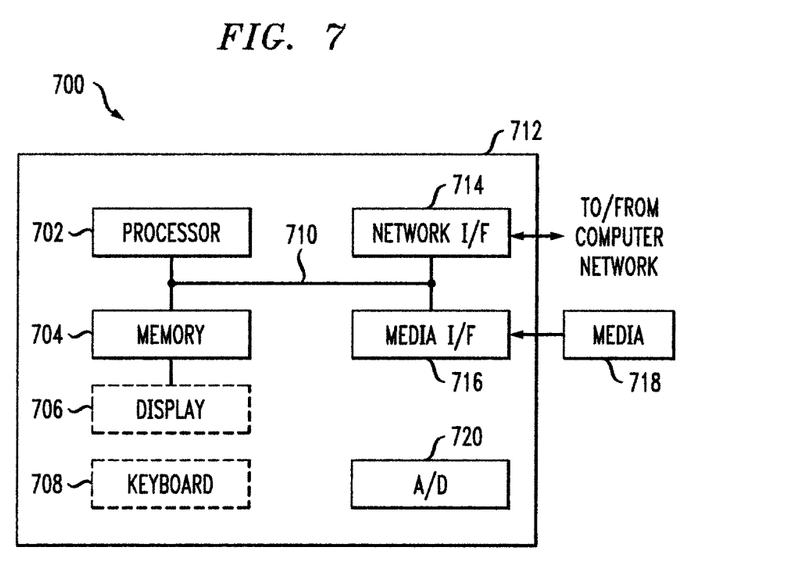
FIG. 7 depicts an exemplary aggregation and visualization system that may be useful in implementing one or more aspects and/or elements of the present invention.

According to one aspect of the invention, temporal event data extracted from multiple records is summarized to show aggregate evolution statistics for a number of records. Another aspect of the invention aggregates the temporal event data, such as multiple patient records, into a graph-based visual presentation. In this manner, aspects of the present invention allow desirable pathways to be identified that should be encouraged, and as well as undesirable pathways that should be avoided. In one exemplary embodiment, the disclosed aggregation and visualization system 700 aggregates temporal event data from a number of patients and visualizes alternative clinical pathways using coded edges, such as color-coded edges, that map to patient outcome. Another aspect of the invention provides interactive capabilities to allow users to explore the data and uncover insights. Thus, users can optionally manipulate the visualization through direct interaction techniques (e.g., selection and brushing) and a series of control widgets.

The present invention is illustrated using an exemplary diagnosis of congestive heart failure (CHF). Congestive heart failure is generally defined as the inability of the heart to supply sufficient blood flow to meet the needs of the body. CHF is difficult to manage and there is no accepted system of diagnostic criteria. One commonly used system comes from the Framingham study. See, e.g., P. A. McKee et al., "The Natural History of Congestive Heart Failure: the Framingham Study," The New England J. of Medicine, 285(26):1441-46 (1971). Generally, the Framingham diagnosis system requires the simultaneous presence of at least two major symptoms (e.g., S3 gallop, Acute pulmonary edema and Cardiomegaly) or one major symptom in conjunction with two minor symptoms (e.g., Nocturnal cough, Pleural effusion and Hepatomegaly). In total, 18 distinct Framingham symptoms have been defined.

The present invention provides an aggregation and visualization system 700 (discussed further below in conjunction with FIG. 7) that aggregates and/or visualizes temporal event data. The exemplary temporal event data includes time-stamped entries for each time a patient was diagnosed with a Framingham symptom. For example:

Patient#1: (27 Jul. 2009, Ankle edema), (14 Aug. 2009, Pleural effusion), . . .

Patient#2: (17 May 2002, 83 gallop), (1 Feb. 2003, Cardiomegaly), . . . .

In line with the use of Framingham symptoms for diagnosis, an assumption is made that once a symptom has been observed it applies perpetually (i.e., symptoms are accumulative). Thus, the event sequences for each patient can be filtered to select only the first occurrence of a given symptom type. The filtered event sequences describe the flow for each patient through different disease states. For example, a filtered event sequence "symptom A→symptom B" indicates that the patient's flow between states is "no symptom→symptom A symptoms A and B."

The exemplary data also has an outcome for each patient entity using a binary value (e.g., deceased (0) or survivor (1)) or in a normalized range between 0 and 1 to indicate, for example, a quality of life measure. As discussed further below, the aggregate outcome for each node/edge is a function of the outcomes for contained entities, such as the average outcome for all patients in a given disease state.

Figure 1:
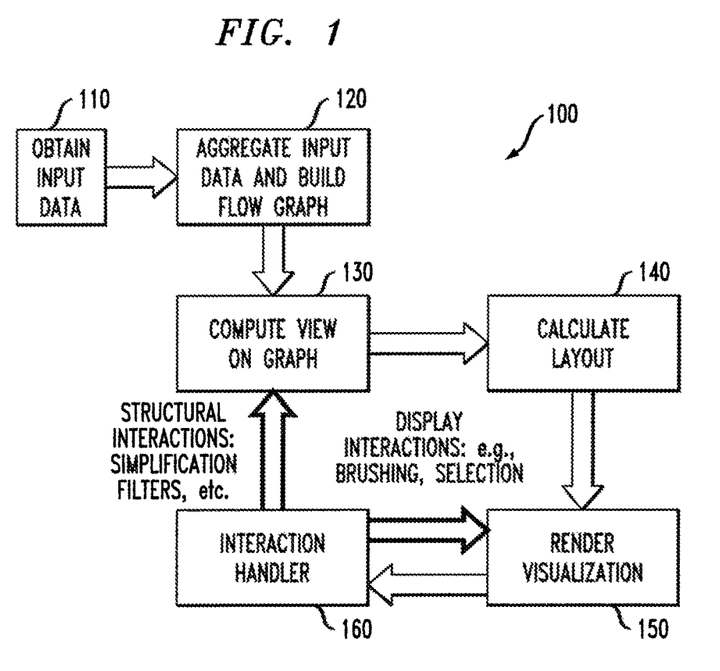
FIG. 1 is a flow chart describing an exemplary implementation of an aggregation and visualization process incorporating aspects of the present invention.

FIG. 1 is a flow chart describing an exemplary implementation of an aggregation and visualization process 100 incorporating aspects of the present invention. As shown in FIG. 1 and as discussed further below in conjunction with FIG. 2, the exemplary aggregation and visualization process 100 initially obtains the input data during step 110. Thereafter, the exemplary aggregation and visualization process 100 aggregates the input data and builds a flow graph during step 120, computes a view on the flow graph during step 130 and calculates a layout during step 140, as discussed further below in conjunction with FIG. 3.

The exemplary aggregation and visualization process 100 then renders a visualization of the aggregated data during step 150, as discussed further below in conjunction with FIGS. 4 through 6. During step 160, an interaction handler interacts with the visualization to display user interactions, such as brushing and selection, and with the flow graph to process structural interactions, such as simplifications and filters to reduce visual clutter, as discussed further below in a section entitled "Interactions and Simplifications."

Figure 2:
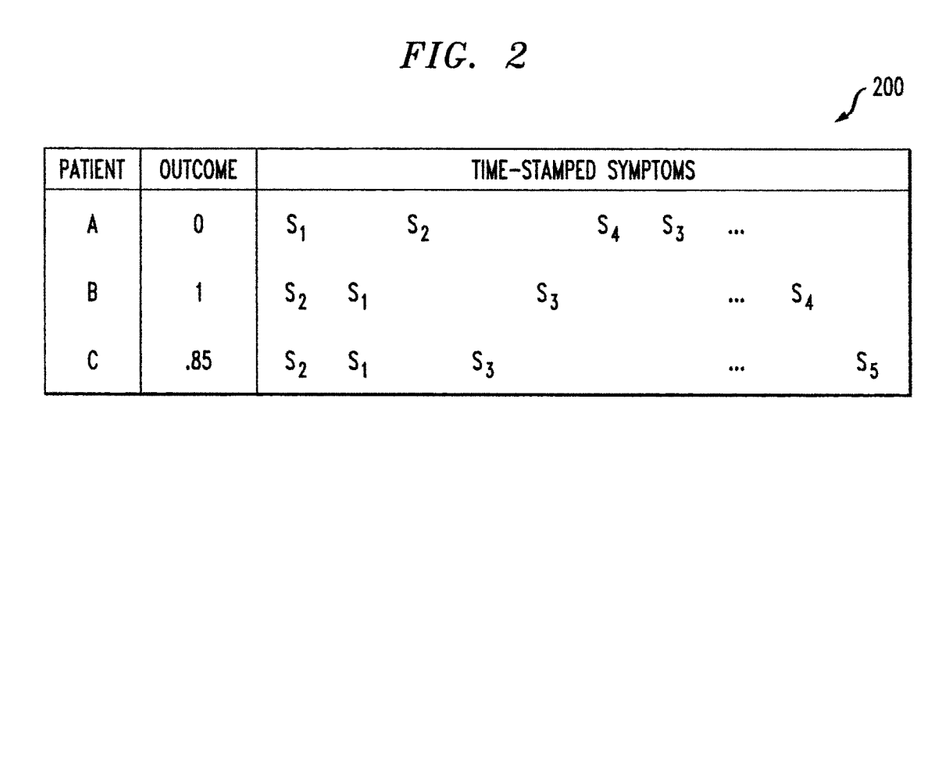
FIG. 2 illustrates exemplary temporal event data.

FIG. 2 illustrates exemplary temporal event data 200. The exemplary temporal event data 200 comprises a plurality of records, each associated with a given patient. Each exemplary patient record comprises a patient identifier, as well as an indication of the outcome and a time-stamped list of the symptoms experienced by the patient.

Figure 3:
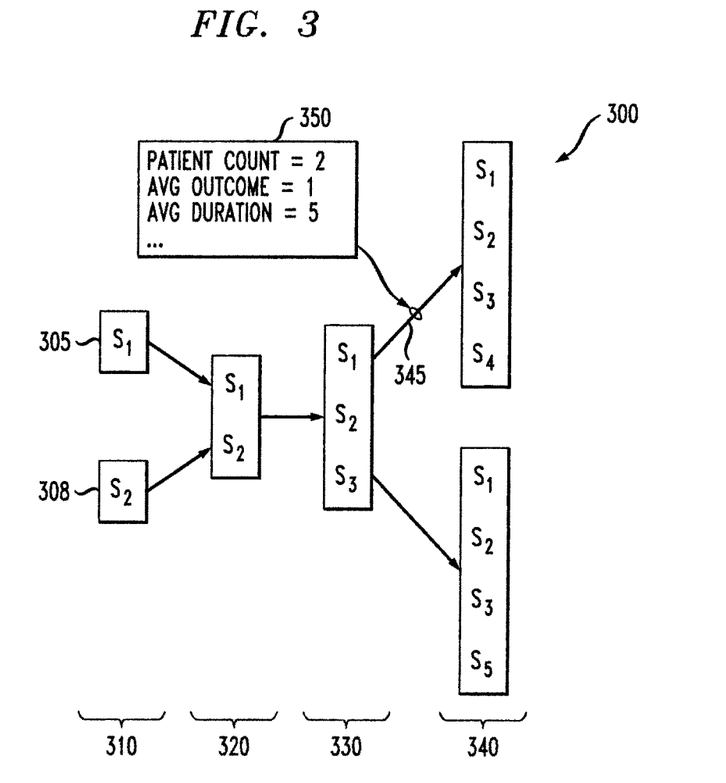
FIG. 3 illustrates a portion of an exemplary flow graph based on an aggregation of the exemplary temporal event data of FIG. 2.

FIG. 3 illustrates a portion of an exemplary flow graph 300 based on an aggregation of the exemplary temporal event data 200 (FIG. 2). The exemplary flow graph 300 is a state diagram represented using a directed acyclic graph (DAG) (e.g., all transitions move left to right). The nodes, such as nodes 305, 308, are a unique combination of symptoms that were observed in the data. The nodes thus represent groups of entities in a given state. Patient statistics are anchored to the flow graph 300 to describe specific patient subpopulations.

The edges, such as edge 345, between states capture symptom transitions. In one exemplary embodiment, each edge, such as edge 345, has an associated annotation 350 with the number of patients that make the corresponding transition, the average time gap between the states, and the average outcome of the patient group.

The exemplary flow graph 300 is sliced vertically into layers 310, 320, 330, 340. A given layer i contains all nodes with i symptoms. The exemplary layers are sorted from left to right, showing information from the past to the future. Generally, the first layer 310 in FIG. 3 contains only two nodes 305, 308, which represent patients that have one symptom, $S_1$ and $S_2$, respectively. The next layer 320 has one node, which represent patients that have both symptom, $S_3$ and $S_2$.

Figure 4:
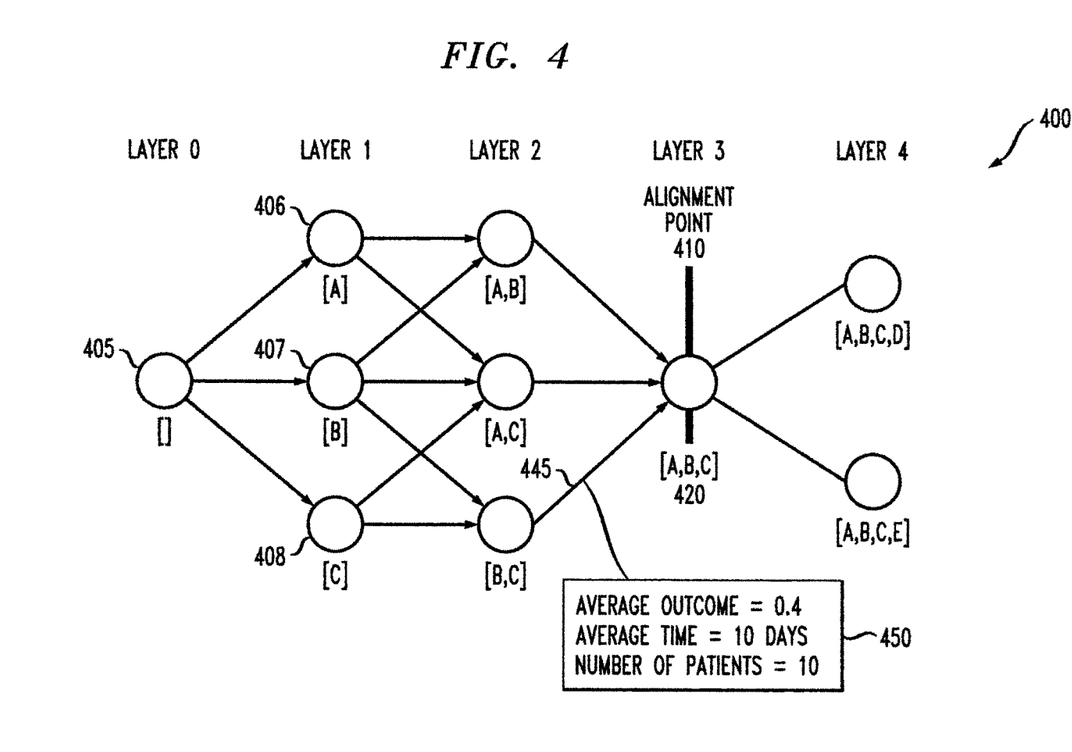
FIG. 4 illustrates a portion of an alternate exemplary flow graph based on an aggregation of the exemplary temporal event data of FIG. 2.

FIG. 4 illustrates a portion of an alternate exemplary flow graph 400 based on an aggregation of the exemplary temporal event data 200 (FIG. 2). The exemplary flow graph 400 of FIG. 4 captures the various event paths that led to an alignment point 410 and all the event paths that occurred after the alignment point 410. The exemplary embodiment of FIG. 4 allows a user to select a target patient from the database 200 and use the current state of the target patient as the alignment point 410. In another application, the alignment point 410 can be used to evaluate a given patient being treated by a physician who has a given set of symptoms. The other patients in the same node have the same symptoms (and possibly more), and the physician can evaluate and prioritize the available outgoing paths to determine a course of treatment, based on the outcomes of the other patients on each outgoing path.

In the embodiment of FIG. 4, each edge, such as edge 445, has an associated annotation 450, in a similar manner to FIG. 3, with the number of patients that make the corresponding transition, the average time gap between the states, and the average outcome of the patient group. In this manner, historical data can be analyzed when considering the possible future progression of symptoms for the selected target patient.

Construction of the flow graph 400 begins by selecting an alignment point 410. For example, a set of patient event sequences can be aligned around a state 420 where all patients have the same three symptoms A, B and C and no other symptoms. After choosing an alignment point 410, the flow graph 400 is constructed using data from all patients that satisfy the alignment point 410, identifying the paths that led to this state 410, and the paths after state 410. In this manner, the exemplary flow graph 400 captures the various event sequences that led to the alignment point 410 and all the sequences that occurred after the alignment point 410.

The nodes, such as node 420, are the unique combinations of symptoms, such as symptoms A, B, C, D and E, that were observed in the data 200. The nodes thus represent groups of entities in a given state. For example, node 405 corresponds to no symptoms. A patient can transition to another node 406-408 having one symptom A, B or C. Edges, such as edge 445, capture symptom transitions.

Edges in the exemplary layout of the flow graphs 300, 400 in FIGS. 3 and 4 can be straightened (to reduce bending of edges), for example, using a force-directed algorithm, where each node is treated as a particle and the total force is the difference between the force from the edges and the repulsion between nodes. In addition, an edge routing algorithm can reduce a number of overlapping edges (which can happen even without crisscrossing due to the thickness of the edges), for example, based on time edge length.

The number of edge crossings in the flow graphs 300, 400 in FIGS. 3 and 4 can be reduced based on, for example, the teachings of K. Sugiyama et al., "Methods for Visual Understanding of Hierarchical System Structures," IEEE Trans. on Systems, Man, and Cybernetics, 11(2), 109-125 (1981), incorporated by reference herein. Generally, the exemplary layouts of the flow graphs 300, 400 in FIGS. 3 and 4 are based on adjacency matrices and barycenter (center of mass).

Figure 5:
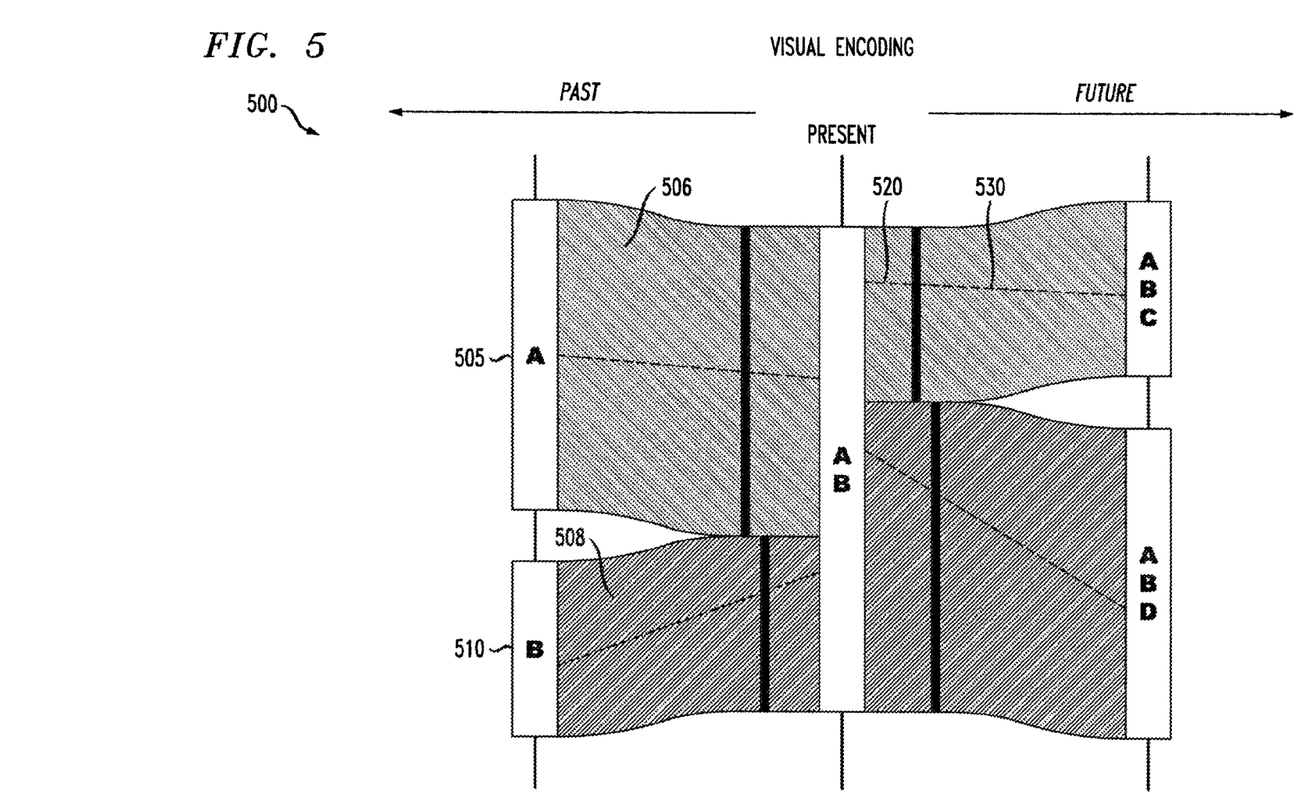
FIG. 5 illustrates a portion of an exemplary visual encoding of the flow graphs of FIGS. 3 and 4.

FIG. 5 illustrates a portion of an exemplary visual encoding 500 of the flow graphs 300, 400 of FIGS. 3 and 4. For example, as shown in FIG. 5, nodes in the flow graphs 300, 400, such as nodes 505, 510 are visually encoded using rectangles while edges are represented using two distinct visual marks: time edges 520 and link edges 530. The average outcome is encoded, for example, using a distinct hash pattern 506, 508 or color (not shown). For example, the color can scale linearly from red to green with red representing the worst outcomes and green representing the best outcomes. The horizontal position of a node 505, 510 indicates a sequence of states.

The height of a node 505, 510 indicates a number of people associated with the node. A time edge 520 is a rectangle and the width of time edge 520 indicates a duration of the corresponding transition. Link edges 530 connect nodes and time edges 520 to convey sequentiality.

In this manner, the exemplary visual encoding 500 indicates (a) the time gap for each state change, (b) the cardinality of patients in each state and state transition, and (c) the average patient outcome for each state and transition. The exemplary visual encoding 500 is based on the teachings of D. Pharm et al., "Flow Map Layout," Proc. IEEE Symp. Information Visualization, 219-224 (2005) and K. Wongsuphasawat et al., "LifeFlow: Visualizing an Overview of Event Sequences," Proc. Annual SIGCHI Conf. Human Factors in Computing Systems (CHI), 1747-1756 (2011), each incorporated by reference herein.

The exemplary visual encoding 500 slices the flow graph vertically into layers. Layer i contains all flow graph nodes with i symptoms. The layers Are sorted from left to right, showing information from the past to the future. For example, in FIG. 5, the first layer (layer 0) contains only one node, which represents patients that have no symptom. The next layer (layer 1) has three nodes, one for each first-occurring symptom in the patient cohort.

An end node (not shown) can be used to indicate a state where the path of each patient stops. The height of the end node can be proportional to the number of patients whose path stops at a given point.

Figure 6:
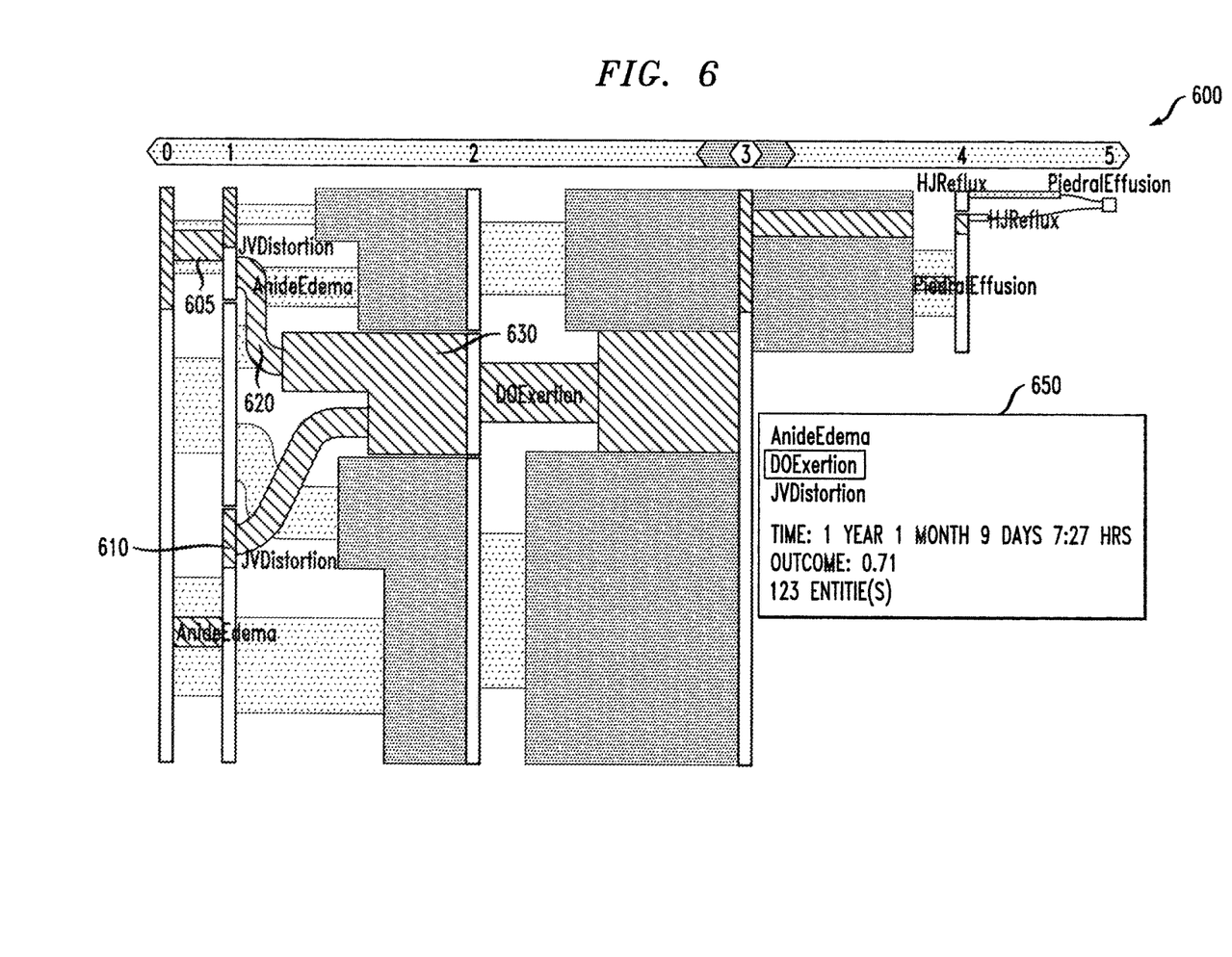
FIG. 6 illustrates an exemplary visual encoding of a flow graph.

FIG. 6 illustrates an exemplary visual encoding 600 of a flow graph 300, 400. As discussed above in conjunction with FIG. 5, nodes in the flow graphs 300, 400, such as nodes 605, 610 are visually encoded using rectangles while edges are represented using two distinct visual marks: time edges 620 and link edges 630. The average outcome is encoded, for example, using a distinct hash pattern or color (not shown). For example, the color can scale linearly from red to green with red representing the worst outcomes and green representing the best outcomes.

The horizontal position of a node 605, 610 indicates asequence of states. The height of a node 605, 610 indicates a number of people associated with the node. The width of time edge 630 indicates a duration of the corresponding transition. Link edges 620 connect nodes and time edges 630 to convey sequentiality.

In the exemplary visual encoding 600 of FIG. 6, each edge has an associated annotation 650, in a similar manner to FIGS. 3 and 4, with the number of patients that make the corresponding transition, the average time gap between the states, the average outcome of the patient group, and, optionally, a listing of the associated symptoms.

As discussed further below, a brushing feature allows a user to hover the mouse over a node or an edge to highlight all paths traveled by patients passing through the corresponding point in the outflow graph. The same brushing feature allows a user to view detailed node information about moused-over nodes and edges via callouts.

Interactions and Simplifications

As discussed above in conjunction with FIG. 1, an interaction handler interacts with the visualization to display user interactions, such as brushing and selection.

To allow interactive data exploration, an exemplary implementation of the aggregation and visualization system 700 allows a user to pan and zoom to uncover detailed structure. In addition. users can filter both nodes and edges based properties. For example, users can filter based on the number of associated patients to remove small subgroups below a specified patient number threshold.

Users can optionally select which symptom types are used to construct the flow graph 300, 400. In this manner, user can omit symptoms that users deem uninteresting. For example, a user can remove Nocturnal Cough if they deem it irrelevant to an analysis and the visualization will be recomputed dynamically.

A brushing feature allows a user to hover the mouse over a node or an edge to highlight all paths traveled by patients passing through the corresponding point in the outflow graph (see FIG. 6). In addition, in an exemplary implementation of the aggregation and visualization system 700, hovering also triggers the display of tooltips 650 that provide more information about individual nodes and edges. Tooltips 650 shows all symptoms associated with the corresponding node/edge, the average outcome, and the total number of patients in the subgroup (see FIG. 6).

As discussed above in conjunction with FIG. 1, an interaction handler interacts with the flow graph to process structural interactions, such as simplifications and filters to reduce visual clutter.

In addition, the aggregation and visualization system 700 optionally permits a user to disable certain event types dynamically. For example, the user can be presented with a list of available event types. For each event type, the user can see the number of events, number of entities within the event type, and a value expressing a correlation between the event type and the outcome.

A clustering feature optionally allows a user to cluster nodes in each layer (e.g., having similar states).

Another aspect of the invention provides an indication of various factors that may be correlated with each state. For example, the factors may include medications and interventions. In this manner, a user can evaluate how a given factor correlates with the outcome. Generally, factors that correlate (positively or negatively) with the sub-population at a given point in the flow can be identified to determine if a particular item (e.g., a specific medication or medical procedure) might be the reason that a group has a good or bad outcome.

Exemplary System and Article of Manufacture Details

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

One or more embodiments of the invention, or elements thereof, can be implemented in the form of an apparatus including a memory and at least one processor that is coupled to the memory and operative to perform exemplary method steps.

One or more embodiments can make use of software running on a general purpose computer or workstation. FIG. 7 depicts an exemplary aggregation and visualization system 700 that may be useful in implementing one or more aspects and/or elements of the present invention. With reference to FIG. 7, such an implementation might employ, for example, a processor 702, a memory 704, and an input/output interface formed, for example, by a display 706 and a keyboard 708. The memory 704 may store, for example, code for implementing the layout process 300 of FIG. 3.

The term "processor" as used herein is intended to include any processing device, such as, for example, one that includes a CPU (central processing unit) and/or other forms of processing circuitry. Further, the term "processor" may refer to more than one individual processor. The term "memory" is intended to include memory associated with a processor or CPU, such as, for example, RAM (random access memory), ROM (read only memory), a fixed memory device (for example, hard drive), a removable memory device (for example, diskette), a flash memory and the like.

In addition, the phrase "input/output interface" as used herein, is intended to include, for example, one or more mechanisms for inputting data to the processing unit (for example, mouse), and one or more mechanisms for providing results associated with the processing unit (for example, printer). The processor 702, memory 704, and input/output interface such as display 706 and keyboard 708 can be interconnected, for example, via bus 710 as part of a data processing unit 712. Suitable interconnections, for example via bus 710, can also be provided to a network interface 714, such as a network card, which can be provided to interface with a computer network, and to a media interface 716, such as a diskette or CD-ROM drive, which can be provided to interface with media 718.

Analog-to-digital converter(s) 720 may be provided to receive analog input, such as analog video feed, and to digitize same. Such converter(s) may be interconnected with system bus 710.

Accordingly, computer software including instructions or code for performing the methodologies of the invention, as described herein, may be stored in one or more of the associated memory devices (for example, ROM, fixed or removable memory) and, when ready to be utilized, loaded in part or in whole (for example, into RAM) and implemented by a CPU. Such software could include, but is not limited to, firmware, resident software, microcode, and the like.

A data processing system suitable for storing and/or executing program code will include at least one processor 702 coupled directly or indirectly to memory elements 704 through a system bus 710. The memory elements can include local memory employed during actual implementation of the program code, bulk storage, and cache memories which provide temporary storage of at least some program code in order to reduce the number of times code must be retrieved from bulk storage during implementation.

Input/output or I/O devices (including but not limited to keyboards 708, displays 706, pointing devices, and the like) can be coupled to the system either directly (such as via bus 710) or through intervening 110 controllers (omitted for clarity).

Network adapters such as network interface 714 may also be coupled to the system to enable the data processing system to become coupled to other data processing systems or remote printers or storage devices through intervening private or public networks. Modems, cable modem and Ethernet cards are just a few of the currently available types of network adapters.

As used herein, including the claims, a "server" includes a physical data processing system (for example, system 712 as shown in FIG. 7) running a server program. It will be understood that such a physical server may or may not include a display and keyboard.

As noted, aspects of the present invention may take the form of a computer program product embodied in one or more computer readable medium(s) having computer readable program code embodied thereon. Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. Media block 718 is a non-limiting example. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless. wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the FIGS. illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

Method steps described herein may be tied, for example, to a general purpose computer programmed to carry out such steps, or to hardware for carrying out such steps, as described herein. Further, method steps described herein, including, for example, obtaining data streams and encoding the streams, may also be tied to physical sensors, such as cameras or microphones, from whence the data streams are obtained.

It should be noted that any of the methods described herein can include an additional step of providing a system comprising distinct software modules embodied on a computer readable storage medium. The method steps can then be carried out using the distinct software modules and/or sub-modules of the system, as described above, executing on one or more hardware processors 502. In some cases, specialized hardware may be employed to implement one or more of the functions described here. Further, a computer program product can include a computer-readable storage medium with code adapted to be implemented to carry out one or more method steps described herein, including the provision of the system with the distinct software modules.

In any case, it should be understood that the components illustrated herein may be implemented in various forms of hardware, software, or combinations thereof; for example, application specific integrated circuit(s) (ASICS), functional circuitry, one or more appropriately programmed general purpose digital computers with associated memory, and the like. Given the teachings of the invention provided herein, one of ordinary skill in the related art will be able to contemplate other implementations of the components of the invention.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:

1. A method for processing temporal event data, comprising the steps of:
   obtaining said temporal event data comprising a plurality of entities undergoing one or more events;
   aggregating said temporal event data;
   generating a flow graph to represent said aggregated temporal event data, wherein said flow graph comprises a directed acyclic graph having a plurality of nodes connected by edges, wherein each of said nodes represents a group of entities in a given state, wherein each edge has an associated annotation indicating a number of entities that make a corresponding transition, an average time gap between states, and an average outcome of the entities that make the corresponding transition;
   generating a view of said flow graph;
   rendering a visualization of said flow graph view to a user;
   obtaining one or more user interactions; and
   updating one or more of said visualization and said flow graph view based on said user interactions.

2. The method of claim 1, wherein said flow graph is sliced into layers, wherein a given layer i contains all nodes with i events.

3. The method of claim 1, wherein said flow graph indicates event paths that lead to a given alignment point and event paths that lead from the alignment point.

4. The method of claim 1, wherein nodes in said visualization are visually encoded using a given shape.

5. The method of claim 1, further comprising the step of straightening one or more edges in one or more of said flow graph and said visualization.

6. The method of claim 1, further comprising the step of reducing a number of overlapping edges in one or more of said flow graph and said visualization.

7. The method of claim 1, further comprising the step of reducing a number of edge crossings in one or more of said flow graph and said visualization.

8. The method of claim 1, wherein said user interactions comprise one or more structural interactions that require an update to said flow graph view.

9. The method of claim 1, wherein said user interactions comprise one or more display interactions that require an update to said visualization.

10. The method of claim 1, further comprising the step of identifying one or more factors that may be correlated with a given state in said flow graph.

11. The method of claim 1, wherein edges in said visualization are visually encoded using at least a time edge and at least a link edge.

12. The method of claim 11, wherein a size of said time edge indicates a duration of a corresponding transition.

13. The method of claim 11, wherein said link edge connects an end of one of said time edges with a node to indicate a sequentiality of nodes.

14. The method of claim 1, wherein an average outcome is encoded using one or more of a distinct hash pattern and a distinct color.

15. The method of claim 14, wherein said distinct color transitions linearly between two values each representing a different extreme outcome.

16. The method of claim 1, wherein a position of a node in one direction indicates a sequence of states.

17. The method of claim 1, wherein a size of a node in one direction indicates a number of entities associated with the node.

18. The method of claim 1, wherein said temporal event data comprises medical data and wherein each of said nodes is a unique combination of symptoms that were observed in the medical data.

19. The method of claim 1, wherein said temporal event data comprises medical data and wherein each of said edges between states capture symptom transitions.

20. The method of claim 1, wherein said view of said flow graph is computed using one or more of simplification and filtering based on user parameters.

21. An apparatus for processing temporal event data, the apparatus comprising:
   a memory; and
   at least one hardware device, coupled to the memory, operative to:
   obtain said temporal event data comprising a plurality of entities undergoing one or more events;
   aggregate said temporal event data;
   generate a flow graph to represent said aggregated temporal event data, wherein said flow graph comprises a directed acyclic graph having a plurality of nodes connected by edges, wherein each of said nodes represents a group of entities in a given state, wherein each edge has an associated annotation indicating a number of entities that make a corresponding transition, an average time gap between states, and an average outcome of the entities that make the corresponding transition;
   generate a view of said flow graph;
   render a visualization of said flow graph view to a user;
   obtain one or more user interactions; and
   update one or more of said visualization and said flow graph view based on said user interactions.

22. The apparatus of claim 21, wherein said user interactions comprise one or more structural interactions that require an update to said flow graph view.

23. The apparatus of claim 21, wherein said user interactions comprise one or more display interactions that require an update to said visualization.

24. An article of manufacture for processing temporal event data, comprising a non-transitory machine readable recordable medium containing one or more programs which when executed implement the steps of:
   obtaining said temporal event data comprising a plurality of entities undergoing one or more events;
   aggregating said temporal event data;
   generating a flow graph to represent said aggregated temporal event data, wherein said flow graph comprises a directed acyclic graph having a plurality of nodes connected by edges, wherein each of said nodes represents a group of entities in a given state, wherein each edge has an associated annotation indicating a number of entities that make a corresponding transition, an average time gap between states, and an average outcome of the entities that make the corresponding transition;
   generating a view of said flow graph;
   rendering a visualization of said flow graph view to a user;

obtaining one or more user interactions; and
updating one or more of said visualization and said flow graph view based on said user interactions.

\* \* \* \* \*